United States Patent
Bru Martinez et al.

(10) Patent No.: US 7,309,591 B2
(45) Date of Patent: Dec. 18, 2007

(54) METHOD FOR THE PRODUCTION OF RESVERATROL IN CELL CULTURES

(75) Inventors: Roque Bru Martinez, Alicante (ES); Maria del los Angeles Pedreno Garcia, Alicante (ES)

(73) Assignee: Universidad de Alicante, Alicante (ES)

( * ) Notice: Subject to any disclaimer, the term of this patent is extended or adjusted under 35 U.S.C. 154(b) by 347 days.

(21) Appl. No.: 10/501,339

(22) PCT Filed: Jan. 21, 2003

(86) PCT No.: PCT/ES03/00026

§ 371 (c)(1), (2), (4) Date: Mar. 30, 2005

(87) PCT Pub. No.: WO03/062406

PCT Pub. Date: Jul. 31, 2003

(65) Prior Publication Data

US 2006/0205049 A1 Sep. 14, 2006

(30) Foreign Application Priority Data

Jan. 24, 2002 (ES) ............... 200200162

(51) Int. Cl.
- *C12P 7/22* (2006.01)
- *C12P 7/00* (2006.01)
- *C12P 7/02* (2006.01)
- *C12P 1/00* (2006.01)

(52) U.S. Cl. ............... 435/156; 435/41; 435/132; 435/155

(58) Field of Classification Search ............ None
See application file for complete search history.

(56) References Cited

OTHER PUBLICATIONS

Bako,P; Fenichel,L; Toke,L; Szente,L; Szejtli,J. "Methylation of Cyclodextrins by Phase-Transfer Catalysis", Journal of Inclusion Phenomena and Molecular Recognition in Chemistry. 1994, 18, 307-314.*

Morales, M. et al., Effect of dimethyl-beta-cyclodextrins on resveratrol metabolism in Gamay grapevine cell cultures before and after inoculation with *Xylophilus ampelinus*, Plant Cell Tissue and Organ Culture, 1998. vol. 53, No. 3, pp. 179-187.

CN 1292415 A (Wei Yahui) Apr. 25, 2001 (Resumen) (en linea) (recuperado el Mar. 4, 2003). Recuperado de EPO EPODOC Database.

* cited by examiner

*Primary Examiner*—Sandra E. Saucier
*Assistant Examiner*—Aaron J Kosar
(74) *Attorney, Agent, or Firm*—Arent Fox, LLP

(57) ABSTRACT

The invention relates to a method for the production of resveratrol in cell cultures. The inventive method consists in: incubating a culture of cells which produce resveratrol naturally, in suspension, in the presence of randomly-methylated β-cyclodextrin (RMBCD) with a degree of substitution of between 11 and 13 under conditions that allow resveratrol synthesis and the excretion of same into the culture medium; and, if desired, isolating the resveratrol produced from said culture medium. The resveratrol can be used in the production of pharmaceutical or nutraceutical products.

6 Claims, 4 Drawing Sheets

METHOD FOR THE PRODUCTION OF RESVERATROL IN CELL CULTURES

FIELD OF THE INVENTION

This invention is related to cell cultures in suspension induced to produce resveratrol, and with culture media that accumulate resveratrol at concentrations greater than its solubility limit. Specifically, the invention is related to the use of randomly methylated cyclodextrins as elicitors of resveratrol synthesis in producing cells in suspension and as accumulators of resveratrol in the culture medium of cells producing and excreting resveratrol. The invention also refers to a procedure for production of resveratrol in cell cultures.

BACKGROUND OF INVENTION

Stilbenoids are biologically active phenolic compounds that exhibit a wide spectrum antibiotic and pharmacological activity.

It is known that certain plants, such as grapevine, can synthesize stilbenoids as an adaptative mechanism in response to a stress, such as ultraviolet irradiation or a microbial infection (Derks et al. 1995. "Stilbene phytoalexins and disease resistance in *Vitis*". In *Handbook of Phytoalexin Metabolism and Action*, M. Daniel and R. P. Purkayastha, eds., Marcel Dekker, Inc. USA, pp. 287-315). One of the main constituents of these compounds is trans-resveratrol or t-resveratrol (trans-3,5,4'-trihydroxystilbene) (Langcake, P. and Pryce, R. J. 1976. "The production of resveratrol by *Vitis vinifera* and other members of the *Vitaceae* as a response to infection or injury", *Physiol. Plant. Pathol.* 9:77-86).

The cis-resveratrol isomer is usually present in extracts from plants producing t-resveratrol and derivative products. Its presence is due to the slow photoisomerization of the trans isomer by irradiation with ultraviolet light (Mattivi, F. et al. 1995. "Isolation, characterization and evolution in red wine vinification of resveratrol monomers" *J. Agric. Food Chem.* 43:1820-1823).

Based on epidemiological and laboratory studies involving humans, animals, animal cells in culture, and enzyme assays, it has been demonstrated that stilbenoids, and particularly resveratrol, have favourable effects on health (Jang, et al. 1997. "Cancer chemopreventive activity of resveratrol, a natural product derived from grapes", *Science* 275:218-220). Therefore, inclusion in human and animal diet of ingestible products containing resveratrol is desirable.

Resveratrol is present in wine and may be implicated in the salutary effects of moderate wine consumption. An increased resveratrol consumption has been proposed as a way for reducing the incidence of cancer and cardiovascular diseases in humans (Soleas, et al. 1997. "Wine as a biological fluid: history, production, and role in disease prevention", *J. Clin. Lab. Anal.* 11:287-313). Resveratrol and plant extracts containing resveratrol have been shown to be effective for the prevention and treatment of arteriosclerosis (Arichi, et al. 1982. "Effect of stilbene components of the roots of *Polygonum cuspidatum* Sieb. et Zucc. on lipid metabolism" *Chem. Pharm. Bull.* 30:1766-1770), as an anti-inflammatory agent (Kimura, et al. 1985. "Effects of stilbenes on arachidonate metabolism in leukocytes" *Biochem. Biophys Acta* 834:275-278), and as an anti-hyperoxidative agent (Kimura et al. 1983. "Effects of stilbene components of roots of *Polygonum* ssp. on liver injury in perodized oil-fed rats" *Planta Medica.* 49: 51-54). Resveratrol has shown a significant inhibition of crypt formation in aberrant colon in a rat model treated with a carcinogenic agent (azoxymethane), thus suggesting its value as a tumour generation inhibitor in humans (Steele et al. 1998. "Cancer chemoprevention drug development strategies for resveratrol", *Pharm. Bio.* 36:62-68 suppl.). Resveratrol has also been reported to promote the formation of nitroxides, which are vasodilating agents and anti-platelet aggregants (Fitzpatrick et al. 1993. "Endothelium-dependent vasorelaxing activity of wine and other grape products" *Am. J. Physiol.* 265: H774-H778).

Considering the beneficial role of resveratrol on human and animal health, it is important to have available an adequate biological source that allows for obtaining resveratrol in adequate amounts to meet the demand. Various studies have been conducted for this purpose.

In a study, whole grapevine plants were treated with aluminium chloride, which acts as an agent eliciting resveratrol synthesis, to increase resveratrol content in the plant and its derivative products, such as grapes, must, and wine (Jeandet et al. "Utilisation du chlorure d'aluminium comme agent éliciteur de la synthése du resvératrol", patent application WO97/18715).

In another study, the resveratrol synthase gene, or a portion thereof, was transferred to a plant not naturally producing resveratrol so that the plant constitutively expresses the gene and accumulates the derivative resveratrol glucoside in its tissues (Hipskind, J. D. "Transgenic plants modified to contain resveratrol glucoside and uses thereof", patent application WO00/44921).

In another study, suspensions of cells from plants producing resveratrol were elicited with portions of fungal cell walls to induce resveratrol synthesis and its accumulation in the culture medium and cells (Liswidowati, et al. 1991. "Induction of stilbene synthase by *Botrytis cinerea* in cultured grapevine cells" *Planta* 183:307-314).

A further study reported the ability of a cyclodextrin, specifically heptakis-(2,6-di-O-methyl-β-cyclodextrin) (DIMEB), to induce in grapevine cell suspensions (*Vitis vinifera* var. Gamay) the synthesis of t-resveratrol, which was excreted into the culture medium (Morales et al. 1998. "Effect of dimethyl-β-cyclodextrins on resveratrol metabolism in Gamay grapevine cell cultures before and after inoculation with *Xylophilus ampelinus*", *Plant Cell Tiss. Org. Cult.* 53:179-187). Cyclodextrins are already known to share the property of increasing the aqueous solubility of poorly water soluble compounds by forming inclusion complexes. Inclusion complexes are formed when a host molecule is housed in the central cavity of the cyclodextrin molecule, the assembly having a similar solubility to free cyclodextrin (Saenger, W. 1980. "Cyclodextrin inclusion compounds in research and industry", *Angew. Chem. Int. Ed. Engl.* 19:344-362). Based on these properties, t-resveratrol excreted by cells can form inclusion complexes with cyclodextrins, and may accumulate in the culture medium at concentrations higher than its aqueous solubility limit without precipitating.

However, various tests conducted by the inventors have demonstrated that, contrary to what could be expected, not all cyclodextrins have the ability to act as elicitors of resveratrol synthesis in cell cultures, and further research is still required in this field.

SUMMARY OF THE INVENTION

The invention addresses the problem of providing a procedure to produce resveratrol in a cell suspension culture.

The solution provided by the invention is based on the identification by the inventors of a cyclodextrin, specifically a randomly methylated β-cyclodextrin (RMBCD) having a high ability to induce the synthesis of resveratrol, particularly t-resveratrol, in producing cells in suspension, and to accumulate the resveratrol excreted into the culture medium. A procedure to produce resveratrol in producing cells in suspension such as the one described in this invention allows for obtaining high amounts of resveratrol, particularly t-resveratrol.

Therefore, an object of this invention is the use of a RMBCD as elicitor of resveratrol synthesis in cells producing resveratrol in suspension, and as accumulator of resveratrol excreted into the culture medium from such cells in suspension.

An additional object of this invention is a method to induce the synthesis of resveratrol in producing cells in suspension by using a RMBCD.

A further object of this invention is a method to accumulate in the culture medium the resveratrol produced and excreted by cells in suspension at concentrations higher than its solubility limit by the addition of a RMBCD to the culture medium.

An additional object of this invention is a procedure for the production of resveratrol, and particularly t-resveratrol, consisting of incubation of cells producing resveratrol in the presence of a RMBCD.

SHORT DESCRIPTION OF FIGURES

FIG. 1 includes chromatograms of the supernatant of a cell culture of *Vitis vinifera* var. Gamay corresponding to the start of incubation and to 96 hours of incubation in a culture medium containing a RMBCD, specifically RAMEB. The UV-vis spectrum of the peaks is simultaneously recorded and compared with the library of authentic standards.

Figure 4:
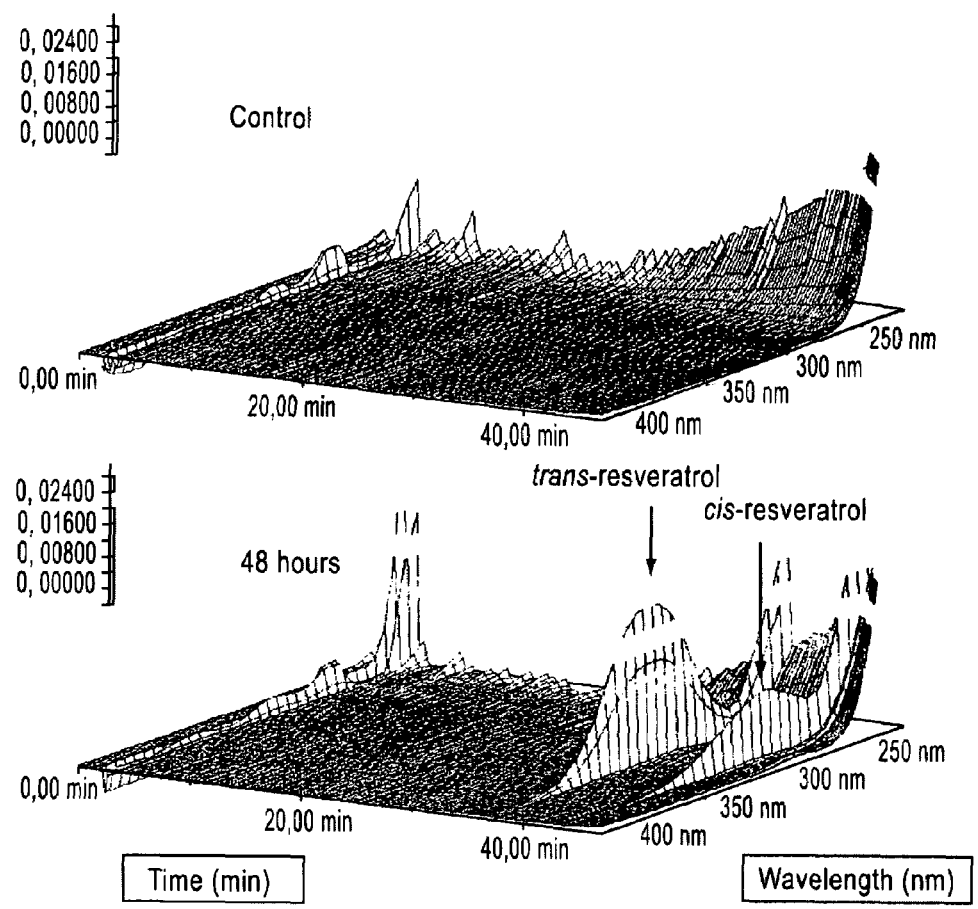

FIG. 4 includes chromatograms of the supernatant of a cell culture of *Vitis vinifera* var. Monastrell corresponding to the start of incubation and to 48 hours of incubation in a medium containing a RMBCD, specifically RAMEB. The UV-vis spectrum of the peaks is simultaneously recorded and compared with the library of authentic standards.

DETAILED DESCRIPTION OF THE INVENTION

The invention relates in general to the use of a cyclodextrin having 7 glucose units, cyclohepta-amylose, randomly methylated with a degree of substitution ranging from 11 to 13, that is, having from 11 to 13 methoxy groups per cyclodextrin ring, as elicitor of resveratrol synthesis in cells naturally producing resveratrol, in suspension, and as accumulator of resveratrol in the culture medium of cells producing resveratrol either naturally or because they have artificially acquired such capacity, and excreting resveratrol, in suspension.

As used in this description, the term "randomly methylated β-cyclodextrin (RMBCD) with a degree of substitution ranging from 11 to 13" refers to a cyclic maltooligosaccharide consisting of 7 D-glucose units bound by type $\alpha(1\rightarrow4)$ glucoside bonds whose hydroxyl groups in positions 2, 3, and 6 of the D-glucose units may be free or derivatized by methylation, such positions carrying methoxy ($CH_3$—O—) chemical groups, with the condition of having 11 to 13 methoxy groups per cyclodextrin ring. In a particular realization, such randomly methylated cyclodextrin contains 12 or 13 methoxy groups per cyclodextrin ring, e.g. a randomly methylated cyclodextrin with a degree of substitution ranging from 12 to 13, identified as RAMEB, having a molecular weight of approximately 1,317, slightly lower than that of DIMEB, approximately 1,331, a β-cyclodextrin consisting of 7 D-glucose units, methylated in all positions 2 and 6 of such glucose units but not in position 3, and thus with a degree of substitution of 14 [see Szejtli J., *Medicinal Research Reviews*, Vol. 14, 3;353-386 (1994), particularly pages 356 and 357, where some characteristics differentiating DIMEB and RAMEB are mentioned]. In another particular realization, such RMBCD contains from 11 to 13 methoxy groups per cyclodextrin ring, such as, for example, the RMBCD with a degree of substitution ranging from 11 to 13 identified as CAVASOL® W7 M (Wacker, Germany), that has a molecular weight of approximately 1,310.

Similarly, as used in this description, the expression "cells naturally producing resveratrol" refers to cells from a plant that naturally has the ability to synthesize resveratrol, such as *Pinus sibirica, Pinus sylvestris, Gnetum parviflorum, Vitis vinifera, Polygonum cuspidatum, Arachis hypogaea, Eucaliptus* sp., *Artocarpus lakoocha, Nothofagus fusca, Phoenix dactilifera, Festuca versuta, Carex fedia, Veratrum grandiflorum*.

In addition, as used in this description, the expression "cells artificially producing resveratrol" refers to cells from an organism that, while not naturally having the ability to synthesize resveratrol, has acquired such ability by means of genetic manipulation processes including transgenesis, such as alfalfa, soy or, in general, any other plant not naturally producing resveratrol.

Moreover, in this invention, unless otherwise stated, the terms "plant" or "organism" include parts, tissues, cells, or protoplasts from the plant or organism, cell cultures, tissue cultures, calluses, embryos, and seeds ultimately coming from the plant or organism.

Therefore, the invention refers in one aspect to a method for inducing the synthesis of resveratrol in a suspension culture of cells naturally producing resveratrol, such method consisting of incubating such cells in the presence of a RMBCD with a degree of substitution ranging from 11 to 13 under conditions that allow for resveratrol synthesis by such cells. In general, any plant naturally producing resveratrol can serve as adequate source for cell lines to be elicited in the synthesis of resveratrol in a cell suspension culture. Incubation conditions (temperature, photoperiod, shaking, auxin/cytokinin hormone ratio, etc.) will depend, among other factors, on the cell lines to be incubated. For illustration purposes only, when such resveratrol-producing cells come from grapevine (*Vitis vinifera*) of the Gamay or Monastrell varieties, they can be cultured in a liquid medium with an intermediate auxin/cytokinin hormone ratio, such as 0.1 mg α-nafthalenacetic acid/0.2 mg kinetin per litre, in the presence of a RMBCD with a degree of substitution ranging from 11 to 13 such as, for instance, the cyclodextrin identified as RAMEB, with 1-2 centimetre orbital shaking at 90-150 rpm, at between 20° C. and 28° C., under a photoperiod of 0 to 16 hours of light (from 8 00 to 5,000 lux) and 8 to 24 hours in the dark, in order to produce resveratrol, particularly t-resveratrol.

In this invention, a culture of cells naturally producing resveratrol is induced under given conditions to synthesize that compound. In the natural induction process, oligosaccharides from the cell was of an invasive fungus elicit the cells from plants naturally producing resveratrol, which start defence mechanisms including, among others, phytoalexin synthesis. In some plant species, the phytoalexins produced are stilbenoid in nature, and specifically, t-resveratrol. In cell cultures, some cyclodextrins (see Example 1) can act as elicitors in the same way as oligosaccharides of the invasive fungus, starting the defence mechanisms of the plant cells leading to the synthesis of t-resveratrol.

As is known, cyclodextrins are compounds with the shape of a truncated cone that have a cavity of a size such as to allow the housing of smaller molecules to form inclusion bodies. The cavity of cyclodextrins is substantially less polar than the aqueous medium, so that the host molecules have a poorly polar nature and, thus, a low solubility in aqueous medium. Cyclodextrins are able to significantly increase the solubility in an aqueous medium of many low polarity compounds. The accepted mechanism for this property is the formation of inclusion complexes, so that the complex has a solubility in an aqueous medium very similar to that of free cyclodextrin. Thus, cyclodextrins can be used to prepare aqueous solutions of compounds with a low polarity at high concentrations. Similarly, cyclodextrins added to a culture medium can increase the solubility of low polarity molecules present in the medium, including those molecules that the cells growing in the medium are able to produce.

Inclusion complexes are in a balance with free cyclodextrin and the free host molecule. Thus, the effects that may be caused by the host molecule on growing cells or the changes the host molecule may experience through the action of chemical, physical, o biological factors of the culture or external to the culture depend on the free form.

The resveratrol synthesized by a cell culture and excreted to the medium containing cyclodextrins can form inclusion complexes with cyclodextrins and eventually accumulate in this way to concentrations similar to that of the cyclodextrin present in the medium.

Accumulation of resveratrol as an inclusion complex with cyclodextrins has many advantages over its free accumulation, including the following: (1) a higher concentration can be achieved in the medium; (2) the complex is more protected from physical-chemical transformations than free resveratrol; and (3) there are less potential effects of back inhibition of resveratrol synthesis by the cells, since the concentration of free resveratrol is lower.

Thus, any cell culture having the ability to produce and excrete resveratrol to the culture medium may benefit from the advantages of including cyclodextrins as resveratrol accumulators in the medium. The procedure for accumulating resveratrol in the culture medium can be applied to any cell suspension producing resveratrol and excreting it to the culture medium, either constitutively or through elicitation.

Therefore, in another aspect, the invention refers to a method to accumulate in a culture medium of cells producing resveratrol either naturally or artificially, in suspension, the resveratrol excreted by such cells at concentrations higher than the solubility limit in such cyclodextrin-free medium. The method consists of adding a RMBCD with a degree of substitution ranging from 11 to 13 to such medium.

The invention also provides a method for producing resveratrol, particularly t-resveratrol, in a culture of cells naturally producing resveratrol in suspension, consisting of incubating such cells in the presence of a RMBCD with a degree of substitution ranging from 11 to 13 under conditions that allow for resveratrol synthesis and excretion into the culture medium and, if desired, for isolating resveratrol from the culture medium.

Any plant naturally producing resveratrol can be used as a source of cell lines for producing resveratrol in a suspension cell culture. The incubation conditions (temperature, photoperiod, shaking, auxin/cytokinin hormone ratio, etc.) will depend, among other factors, on the cell lines to be incubated. For illustration purposes only, when such resveratrol-producing cells come from grapevine (*Vitis vinifera*) of the Gamay or Monastrell varieties, they can be cultured in a liquid medium with an intermediate auxin/cytokinin hormone ratio, such as 0.1 mg α-nafthalenacetic acid/0.2 mg kinetin per litre, in the presence of a RMBCD with a degree of substitution ranging from 11 to 13 such as, for instance, the cyclodextrin identified as RAMEB, with 1-2 centimetre orbital shaking at 90-150 rpm, at between 20° C. and 28° C., under a photoperiod of 0 to 16 hours of light (from 800 to 5,000 lux) and 8 to 24 hours in the dark, in order to produce resveratrol, particularly t-resveratrol.

Resveratrol may be identified by chemically analyzing a part of the cell culture, such as the biological material or the culture medium, using conventional chemical methods, e.g. by organic extraction followed by high performance liquid chromatography (HPLC), gas chromatography (GC) alone or followed by mass spectrometry (GCMS), or capillary electrophoresis (CE).

Resveratrol may be isolated from a part of the cell culture using conventional methods, e.g. by extraction with organic solvents such as diethyl ether or methanol. Alternatively, a part of the cell culture producing resveratrol may also be used in fresh, frozen, or dehydrated form.

Production of resveratrol using a culture of cells naturally producing resveratrol provides advantages over other known production methods, such as those based on extraction from plants or parts of plants that produce resveratrol naturally or by transgenesis, or those based on its chemical synthesis. Such advantages include: (1) the cell culture specifically produces the t-resveratrol isomer, and no other compounds of a phenolic nature are seen, though this isomer may experience photoisomerization; (2) production by culture is not subject to the seasonal or climatic limitations associated to cultivated plants; (3) resveratrol is naturally produced by cells, which increases consumer satisfaction and is more friendly to the environment than the resveratrol produced by chemical synthesis; and (4) as opposed to production of resveratrol by genetically manipulated organisms, the producing culture can be a natural strain, which is usually better accepted by the consumer.

Resveratrol may be isolated from the culture to be used as a crude extract or as purified compound. Administration to humans or animals of resveratrol produced by a cell culture has therapeutic and nutraceutical effects including, but not limited to, the benefits provided by an antioxidant, a platelet aggregation inhibitor, an inhibitor of arachidonate metabolism, a protein kinase inhibitor, an inducer of cell death by apoptosis in tumoral cells, an estrogen receptor antagonist, a ribonucleotide reductase inhibitor, an inhibitor of tumour start, an inhibitor of tumour promotion, an inhibitor of tumour progression and differentiation, an inhibitor of cyclooxigenase-2 and its induction, a modulator of lipoprotein synthesis and release, and a compound with other beneficial effects. The resveratrol produced by a cell culture is also useful as a protector against ultraviolet radiation, a stabilizer of biocontrol agents against damage induced by ultraviolet radiation, and an agent in storage of photochemical energy. Based on the role of resveratrol to confer plants resistance to fungal pathogens, the resveratrol produced by a cell culture could also have application as an antifungal and antibacterial agent in humans.

The resveratrol produced by induced cells and accumulated in the medium is useful for improving human and animal nutrition. Parts of the culture rich in resveratrol may be used as food for humans and animals. Resveratrol-enriched edible compositions may also be obtained by incorporating parts of the culture or resveratrol isolated from the culture. Compositions adequate to be administered as food, nutritional supplement, animal nutritional supplement, nutraceutical, drug, or cosmetic may also be obtained by incorporating parts of the culture or resveratrol isolated from the culture. Resveratrol isolated from the culture or parts thereof may be use for preparing a nutraceutical preparation to achieve a nutritional effect, or for preparing a pharmaceutical product to achieve a therapeutic effect.

The following examples are used to illustrate the invention and should not be considered as limiting its scope.

EXAMPLE 1

Production of Resveratrol in Grapevine Cells in Suspension in the Presence of Cyclodextrins Plant Material and Culture Conditions Grapevine cells (*Vitis vinifera*) from the Gamay rouge, Monastrell albino, and Monastrell green varieties have been used. The characteristics and conditions of culture of the plant material used are mentioned below.

*Vitis vinifera* var. Gamay rouge: A grapevine cell line established by J. C. Pech in 1978 (ENSAT, Toulouse, France) from immature fruits of grapevine from the cultivar Gamay Fréaux has been used. The calluses were kept in 250 ml flasks containing 80 ml of Gamborg $B_5$ basal medium (Gamborg et al. 1968. *Experimental Cell Research* 50:151-158) supplemented with Morel vitamins (Morel, G. 1970. "Le probléme de la transformation tumorale chez les végétaux". *Physiologie Végétale*, 8:189-204), casein hydrolysate (0.25 g/l), saccharose (20 g/l) as carbonated source, and α-nafthalenacetic acid (0.1 mg/l) and kinetin (0.2 mg/l) as hormones (hereinafter, medium). This medium is adjusted to pH 6 and sterilized by applying humid heat (autoclave) for 20 min at a pressure of 121.2 kPa (1.2 athm), acquiring a solid consistency by the addition of purified agar (8 g/l) when the medium is cooled. Cell suspensions were started, from friable calluses obtained in the above described medium, in 250 ml flasks containing 80 ml of agar-free medium. The cells in liquid medium were kept in an orbital shaker at 100 rpm and 25° C., under a photoperiod of 14 hours of light (6 W/m$^2$) and 10 h in the dark.

*Vitis vinifera* var. Monastrell: Two grapevine cell lines of cultivar Monastrell, one established in the dark (albino line) and another established in the presence of white light (green line) from immature fruits have been used. All manipulations and incubations for the green line were carried out in lighting conditions, but for the albino line, incubations for callus generation, development, and growth, as well as incubations of cell suspensions, were performed in the dark. For this, immature grapes approximately 5 mm in diameter were superficially sterilized by immersion in a 7% calcium hypochlorite solution for 15 minutes. After this time, and always under sterile conditions, grapes were washed 3 times with sterile bidistilled water, their seeds removed, and were divided into 4 portions. These portions (explants) were deposited until microcalluses appeared in a Petri dish containing a solid culture medium based on the medium reported by Murashige and Skoog (Murashige, T and Skoog, F. 1962. "A revised medium for rapid growth and bioassays with tobacco tissue cultures". *Physiologia Plantarum* 15:473-497), supplemented with Morel vitamins, casein hydrolysate (0.25 g/l), saccharose (30 g/l) as carbonated source, and α-nafthalenacetic acid (0.1 mg/l) and kinetin (0.2 mg/l) as hormones, 8 g/l of purified agar, and adjusted to pH 6. Finally, these microcalluses were transferred to 250 ml flasks containing 80 ml of this same solid culture medium for callus development. Cell suspensions were started, from friable calluses, in 250 ml flasks containing 80 ml of Gamborg $B_5$ basal medium, supplemented with Morel vitamins, casein hydrolysate (0.25 g/l), saccharose (20 g/l) as carbonated source, and α-nafthalenacetic acid (0.1 mg/l) and kinetin (0.2 mg/l) as hormones, in the absence of agar. The cells in liquid medium were kept in an orbital shaker at 100 rpm and 25° C.; the green line was submitted to a photoperiod of 14 hours of light (6 W/m$^2$) and 10 h in the dark, whereas the albino line was kept in the dark at all times.

Cell Elicitation

For each elicitation experience, 4 g of fresh weight of cells previously washed with fresh medium and filtered were taken under sterile conditions. These cells were transferred to 50 ml flasks and replaced by the addition of 10 ml of sterile fresh medium supplemented in each case with the cyclodextrins stated below:

| Cyclodextrin | Concentration in medium (g/l)* |
|---|---|
| DIMEB | 66.5 |
| HYPROB | 69.0 |
| MALTOYIL | 72.8 |
| Iso P | 91.0 |
| SULFOB | 92.6 |
| BETA | 17.0 |
| RAMEB | 65.8 |
| CAVASOL ® W7 M | 65.5 |

*These concentrations in g/l correspond to concentrations of 50 mmol/liter according to the respective molecular weights, except for BETA, for which the concentration corresponds to 15 mmol/liter due to its lower solubility.
DIMEB: Heptakis (2,6-di-O-methyl)-β-cyclodextrin from CYCLOLAB, Hungary
HYPROB: (2-hydroxy) propyl-β-cyclodextrin with a degree of substitution 5 to 6 from ALDRICH, Spain
MALTOSYL: Maltosyl-β-cyclodextrin with a degree of substitution 1 from BICO, Japan
Iso P: Isoeleat P-trade name of a poorly purified product with a cyclodextrin content >80%, of which Maltosyl-cyclodextrin >50% from BICO, Japan
SULFOB: sulphated β-cyclodextrin sodium salt from ALDRICH, Spain
BETA: β-cyclodextrin or cyclohepta-amylose from SIGMA, Spain
RAMEB: Randomly methylated β-cyclodextrin with a degree of substitution 12 to 13 from CYCLOLAB, Hungary
CAVASOL ® W7 M: Randomly methylated β-cyclodextrin with a degree of substitution 11 to 13 from WACKER, Germany The flasks were incubated under the same conditions as described above for time periods ranging from 24 and 96 hours.

Analysis of Trans-Resveratrol in the Extracellular Medium

Once the incubation time had been completed, the cells were separated from the medium by filtration by making a slight vacuum with the help of a water pump, and the cells and the filtrate were separately collected.

Figure 1:
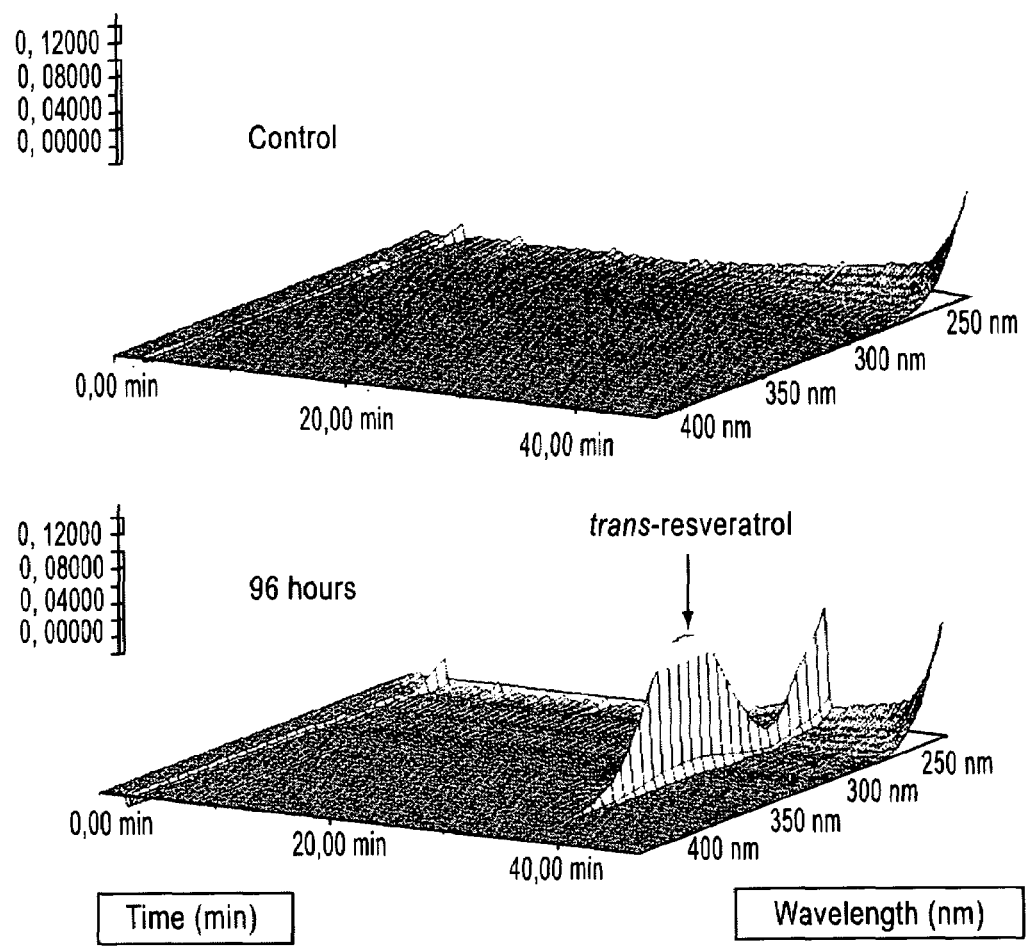

Trans-resveratrol has been shown to be the only species in the filtrate that absorbs light at 306 nm, as detected by HPLC testing (LaChrom, Merck-Hitachi), on line recording of the spectra of chemical species by diode array detector (L-7450), and comparison with a library of phenolic compounds constructed under the same conditions. For this, an aliquot of the filtrate was diluted in fresh medium, filtered through a 0.2 μm Anopore filter, and 20 μl of filtrate were injected in a LiChrospher 100 RP-18 column (250×4 mm, particle size 5 μm). Two types of solvents were used as mobile phase: solvent A, 0.05% trifluoroacetic acid in water, and solvent B, 0.05% trifluoroacetic acid in methanol: acetonitrile 60:40 vol/vol. The sample is eluted at a flow rate of 1 ml/min of the following solvent mixture: 0 min, 10% B; 5 min, 15% B; 40 min, 35% B; 45 min, 65% B; 50 min, 65% B; 55 min, 10% B; and at a column temperature of 35° C. (Dalluge et al., 1998. *J. Chromatogr.* A 793:265-274). FIG. 1 shows the result of this analysis made with the supernatant of a cell culture of *Vitis vinifera* var. Gamay corresponding to the start of incubation and to 96 hours of incubation in a culture medium containing RAMEB.

Figure 2:
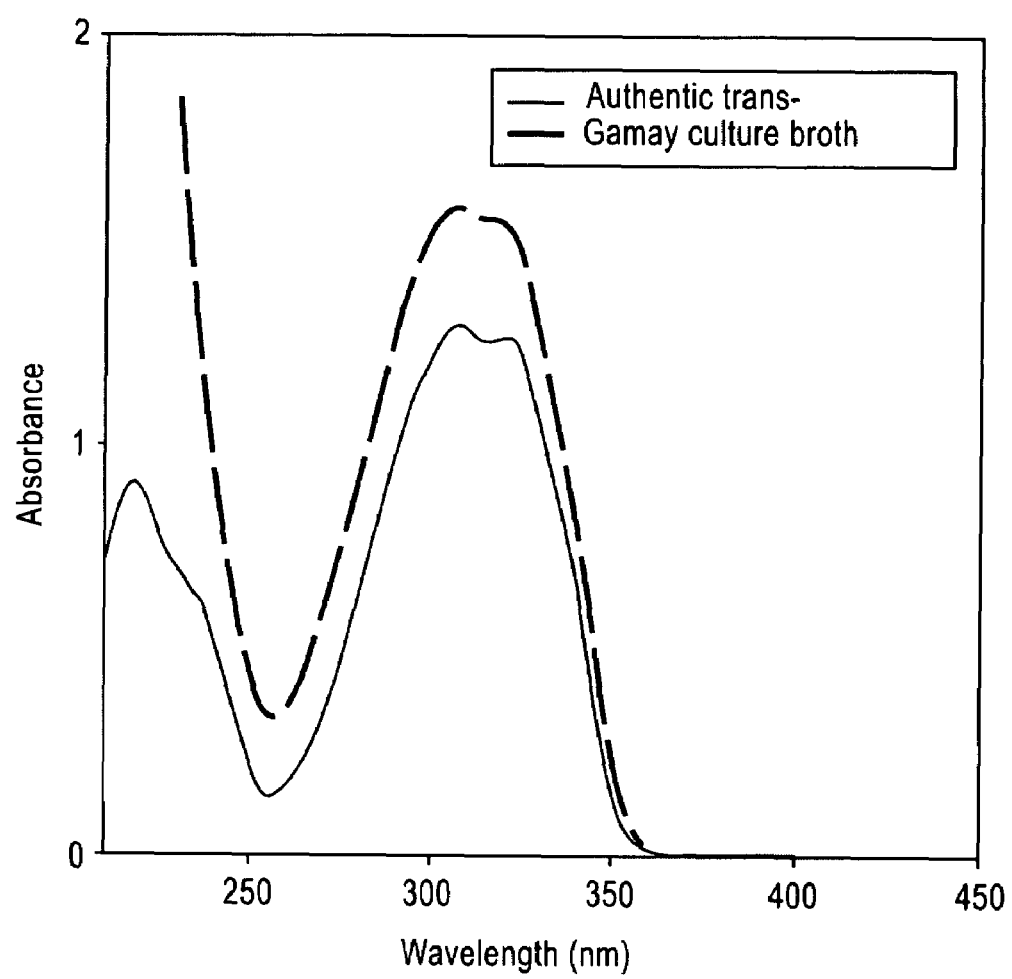
FIG. 2 shows the UV-vis spectrum of authentic t-resveratrol and the supernatant of a cell culture of *Vitis vinifera* var. Gamay corresponding to the start of incubation and to 96 hours of incubation in a culture medium containing a RMBCD, specifically RAMEB.

For routine analysis of t-resveratrol, an aliquot of the filtrate was diluted with fresh medium and its ultraviolet absorption spectrum was recorded using a Kontron Uvikon 940 spectrophotometer taking as reference the fresh medium. The concentration of t-resveratrol in the supernatant was estimated using a molar extinction coefficient at 306 nm of 26,800 $M^{-1}$ $cm^{-1}$ (Siemann, E. H. and Creasy, L. L. 1992, "Concentration of the phytoalexin resveratrol in wine", *Am. J. Enol. Vitic.* 43:49-52). FIG. 2 shows the UV spectrum of a solution of authentic t-resveratrol (Sigma) and supernatant from a cell culture of *Vitis vinifera* var. Gamay corresponding to the start of incubation and to 96 hours of incubation in a culture medium containing RAMEB.

Figure 3:
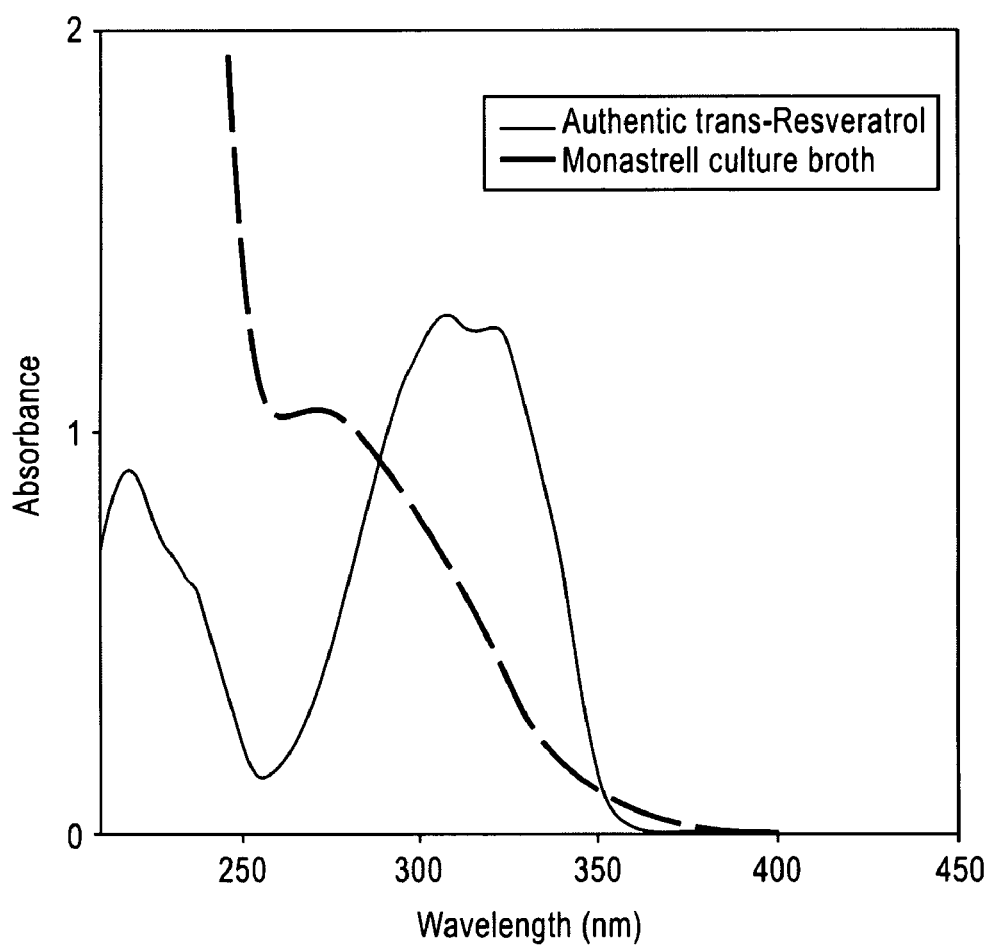
FIG. 3 shows the UV-vis spectrum of authentic t-resveratrol and the supernatant of a cell culture of *Vitis vinifera* var. Monastrell corresponding to the start of incubation and to 48 hours of incubation in a culture medium containing a RMBCD, specifically RAMEB.

FIG. 3 shows the UV-vis spectrum of pure authentic t-resveratrol (Sigma) and supernatant from a cell culture of *Vitis vinifera* var. Monastrell corresponding to the start of incubation and to 48 hours of incubation in a culture medium containing RAMEB. Such FIG. 3 shows significant differences from the spectrum of pure trans-resveratrol. This result suggests that other compounds in addition to trans-resveratrol may be accumulating. Therefore, a qualitative and quantitative analysis of phenolic compounds has been performed by separation, identification, and quantification by HPLC of such compounds. FIG. 4 shows the result of this analysis on the supernatant from a cell culture of *Vitis vinifera* var. Monastrell corresponding to the start of incubation and to 48 hours of incubation in a medium containing RAMEB.

Production and Accumulation of Resveratrol by Grapevine Cells (*Vitis vinifera*) in Suspension in the Presence of Various Cyclodextrins The results obtained, expressed as mg of t-resveratrol per litre of filtrate, eliciting the cells with different cyclodextrins at concentrations of 50 mmol/litre of culture medium (except for BETA, for which the concentration corresponds to 15 mmol/litre due to its lower solubility), after 96 hours of incubation are given in Table 1.

TABLE 1

Milligrams of resveratrol per liter of filtrate of the culture of grapevine cells elicited with various cyclodextrins after 96 hours of incubation

| Type of cyclodextrin | [cyclodextrin] in the medium (g/l)* | Trans-Resveratrol (mg/l) | | |
|---|---|---|---|---|
| | | Gamay Rouge** | Monastrell albino | Monastrell green*** |
| DIMEB | 66.5 | 3060 | 4680 | 90 |
| HYPROB | 69.0 | 990 | 4110 | 90 |
| MALTOSYL | 72.8 | 390 | 660 | 20 |
| Iso P | 91.0 | 240 | 810 | 30 |
| SULFOB | 92.6 | 0 | 0 | 0 |
| BETA | 17.0 | 30 | 60 | 0 |
| RAMEB | 65.8 | 3320 | 5027 | 101 |
| CAVASOL ® W7 M | 65.5 | 3280 | 4963 | 92 |

*These concentrations in g/l correspond to concentrations of 50 mmol/liter according to the respective molecular weights, except for BETA, for which the concentration corresponds to 15 mmol/liter due to its lower solubility.
**Occasional presence of other unidentified phenolic products
***Heavy presence of cis-resveratrol The results obtained demonstrate that RMBCDs, specifically RAMEB and CAVASOL® W7 M, have a greater capacity to induce the synthesis of t-resveratrol in grapevine cells in suspension than any other of the cyclodextrins tested, some of which do not even cause the eliciting effect of t-resveratrol synthesis, while others such as SULFOB are even toxic and kill the cells. It is also noted that the intensity of the effect depends on the variety and the cell line (greater production is seen in the albino Monastrell variety than in the green Monastrell variety).

Solubility of T-Resveratrol in an Aqueous Medium

Five millilitres of a 11,410 mg/l solution of t-resveratrol (99% pure according to the supplier; Sigma, Madrid) in ethanol were placed in an spherical bottle, and ethanol was evaporated to dryness with a $N_2$ current. Residual ethanol was eliminated by keeping the bottle under low pressure overnight. Five millilitres of aqueous medium were added to the solid residue, and the bottle was tightly closed and kept under shaking at 25° C. for 5 days in the dark. The resulting suspension was filtered through 0.2 μm Anopore filters, and the concentration of t-resveratrol in the filtrate was analyzed by UV spectroscopy.

The concentration of t-resveratrol in the filtrates, expressed as mg of t-resveratrol per litre of filtrate, is given in Table 2.

TABLE 2

Solubility of t-resveratrol in an aqueous medium

| Aqueous medium | mg t-resveratrol/liter filtrated |
|---|---|
| Ultrapure water | 36.5 |
| Culture medium | 48.8 |
| Culture medium supplemented with 6.55 mg/ml of DIMEB | 735 |
| Culture medium supplemented with 6.55 mg/ml of RAMEB | 786 |
| Culture medium supplemented with 6.55 mg/ml of CAVASOL ® W7 M | 767 |

The invention claimed is:

1. A method for producing trans-resveratrol, by inducing the synthesis of or by accumulating trans-resveratrol in a culture of cells that naturally produce trans-resveratrol, consisting of incubating the cells in suspension in a culture medium in the presence of a randomly methylated β-cyclodextrin (RMBCD) with a degree of substitution ranging from 11 to 13 under conditions that allow for trans-resveratrol synthesis and excretion into the culture medium and isolating the trans-resveratrol from the culture medium.

2. The method according to claim 1, in which the cells that naturally produce trans-resveratrol are selected from the group consisting of *Pinus sibirica, Pinus sylvestris, Gnetum parviflorum, Vitis vinifera, Polygonum cuspidatum, Arachis hypogaea, Eucaliptus* sp., *Artocarpus lakoocha, Nothofagus fusca, Phoenix dactilifera, Festuca versuta, Carex fedia,* and *Veratrum grandiflorum.*

3. The method according to claim 1, in which the RMBCD with a degree of substitution ranging from 11 to 13 is a cyclic maltooligosaccharide consisting of 7 D-glucose units bound by α(1→4) glucoside bonds and whose hydroxyl groups in positions 2, 3, and 6 of the D-glucose units may be free or derivatized by methylation, and having 11 to 13 methoxy groups per cyclodextrin ring.

4. The method according to claim 3, in which the RMBCD with a degree of substitution ranging from 11 to 13 is the randomly methylated β-cyclodextrin having a degree of substitution ranging from 12 to 13 (RAMEB) or is CAVASOL® W7 M.

5. The method according to claim 1, in which the cells producing trans-resveratrol are cells from *Vitis vinfera*, wherein the culture medium comprises a liquid medium, with an auxin and cytokinin hormone, in the presence of the RMBCD with a degree of substitution ranging from 11 and 13, and wherein the incubation is performed with orbital shaking, at a temperature ranging from 20° C. to 28° C., and under a photoperiod of 0 to 16 hours of light and 8 to 24 hours in the dark.

6. The method according to claim 5 wherein the auxin is α-naphthaleneacetic acid and the cytokinin is kinetin.

* * * * *